United States Patent
Kondo et al.

[11] Patent Number: 5,662,116
[45] Date of Patent: Sep. 2, 1997

[54] MULTI-PLANE ELECTRONIC SCAN ULTRASOUND PROBE

[75] Inventors: Mituo Kondo; Kenji Abe, both of Omiya; Hisashi Nakamura; Yasutaka Nagai, both of Otawara, all of Japan

[73] Assignees: Fuji Photo Optical Co., Ltd., Omiya; Kabushiki Kaisha Toshiba, Kawasaki, both of Japan

[21] Appl. No.: 712,263

[22] Filed: Sep. 11, 1996

[30] Foreign Application Priority Data

Sep. 12, 1995 [JP] Japan .................... 7-258313
Feb. 28, 1996 [JP] Japan .................... 8-065164

[51] Int. Cl.⁶ .................................................. A61B 8/12
[52] U.S. Cl. ........................... 128/662.06; 128/660.1
[58] Field of Search ................... 128/660.01, 660.09, 128/660.1, 662.03, 662.06, 916

[56] References Cited

U.S. PATENT DOCUMENTS

| | | | |
|---|---|---|---|
| 4,841,979 | 6/1989 | Dow et al. | 128/660.1 |
| 4,967,752 | 11/1990 | Blumenthal et al. | 128/660.1 |
| 5,152,294 | 10/1992 | Mochizuki et al. | 128/660.1 X |
| 5,255,684 | 10/1993 | Rello | 128/662.06 |
| 5,377,685 | 1/1995 | Kazi et al. | 128/662.06 |
| 5,413,107 | 5/1995 | Oakley et al. | 128/662.06 |
| 5,456,258 | 10/1995 | Kondo et al. | 128/662.06 |
| 5,469,852 | 11/1995 | Nakamura et al. | 128/662.06 |

*Primary Examiner*—Francis Jaworski
*Attorney, Agent, or Firm*—Oblon, Spivak, McClelland, Maier & Neustadt, P.C.

[57] ABSTRACT

A multi-plane electronic scan ultrasound probe having a rotary member rotatably mounted on a distal end portion of an elongated catheter member of the probe and support thereon an ultrasound transducer consisting of a row of a large number of ultrasound elements. The rotary member is connected to a rotation control knob on a manipulating head of the probe by way of rotation transmission wires extended through the catheter member and via a drive pulley mounted on the manipulating head in association with the rotation control knob to turn the ultrasound transducer through an arbitrary angle in multi-plane electronic scanning by manipulation of the rotation control knob. In addition, for the purpose of tilting the ultrasound transducer through a desired angle, the ultrasound probe is provided with a tilting mechanism to tilt the rotational axis of the rotary member in a predetermined direction, including a tiltable support for the rotary member, a tilt control means provided on the manipulating head, and a tilt signal transmission means for transmitting a tilt control signal from the tilt control means to the tiltable support.

8 Claims, 10 Drawing Sheets

MULTI-PLANE ELECTRONIC SCAN ULTRASOUND PROBE

BACKGROUND OF THE INVENTION

1. Field of the Art

This invention relates to an ultrasound probe, and more particularly to a multi-plane electronic scan ultrasound probe capable of multi-plane electronic scanning through rotations of an ultrasound transducer.

2. Prior Art

In the field of ultrasound probes which have an ultrasound transducer on a distal end portion of an elongated catheter-like insertion member to be introduced into an internal canal or other intracavitary regions of interest, there have been known in the art the so-called multi-plane electronic scanning type ultrasound probes, for example, as described in Japanese Laid-Open Patent Specification S59-22534. More specifically, as seen in FIG. 1 of the published specification, this prior art ultrasound probe has an ultrasound transducer T mounted on a rotary member R within a dome-like casing D on a distal end section of a catheter member C, the ultrasound transducer T consisting of a large number of piezoelectric ceramic transducer elements P which are arranged in a row on the rotary member R. These transducer elements P are driven successively with a predetermined time lag from one another for an electronic linear or sectoral scan over a certain range through an intracorporeal region to be examined. By turning the rotary member R in the arrowed directions in the drawing, one can obtain tomographic ultrasound images on a number of different scanning lines or planes. For instance, in the case of cardiac ultrasound scanning from the alimentary canal, while holding the distal end portion D of the catheter member C in an opposing position within the alimentary canal, the rotary member R is turned around to make scans from different angles. The multi-plane ultrasound scanning of this sort makes it possible to grip the whole image of the heart, and even to display the image of the heart three-dimensionally after voxel data processing by image processing means.

In this connection, there has been a problem that the catheter member, especially the distal end portion of the catheter member becomes objectionably bulky in diameter when a rotational drive mechanism for the rotary member is incorporated into the casing of the distal end portion to rotate an ultrasound transducer with the rotary member. As a countermeasure for this problem, it has been the general practice to drive the rotary member by remote control from a rotational drive mounted on a manipulating probe head which is connected to the proximal end of the catheter member, transmitting rotation from the rotational drive to the rotary member at the distal end of the catheter member through rotation transmission wires. In this regard, for example, a rotational drive mechanism suitable for the remote control of the rotary member is proposed in Japanese Laid-Open Patent Specification H6-261903. Schematically shown in FIG. 2 is the general layout of the prior art ultrasound probe employing a distal end portion and a manipulating probe head as shown in sections in FIGS. 3 and 4, respectively.

More specifically, indicated at 1 in FIG. 2 is an ultrasound probe itself which is largely constituted by a manipulating probe head 2 and a catheter member 3 which is extended out from the manipulating probe head 2. On the side away from the catheter member 3, a cable 4 is led out from the manipulating probe head 2. The cable 4 is provided with a connector 5 at its proximal end for connection to an ultrasound image observation terminal with a monitor screen. The catheter member 3 has a flexible elongated body 3a of a predetermined length, with an angle section 3b and a distal end section 3b successively connected to the fore end of the flexible body 3a.

As seen in FIG. 3, the distal end section 3c of the catheter member 3 is provided with a casing 10 which internally defines a chamber 10a to accommodate an ultrasound transducer 11. This ultrasound transducer 11 is substantially of the same construction as the one shown in FIG. 1, so that details in this regard are omitted from description and drawings to avoid repetitions. The ultrasound transducer 11 is mounted on a follower pulley 12 which serves as a rotary member. In this case, the ultrasound transducer 11 is mounted on packing material 13 which is fixed on the follower pulley 12. Through an acoustic matching layer 14, an acoustic lens 15 is mounted on a signal transmission and reception face of the ultrasound transducer 11. The acoustic lens 15 is located face to face with an acoustic window 16 which is fixedly provided on the casing 10 of the distal end portion. The chamber 10a of the casing 10 is hermetically closed and filled with an ultrasound transmissive medium like liquid paraffin or the like. Denoted at 18 is a flat cable which is connected to the ultrasound transducer 11.

Along with the packing material 13, acoustic matching layer 14 and acoustic lens 15, the ultrasound transducer 11 constitutes an ultrasound transducer unit 19 which is integrally mounted on the follower pulley 12 so that the transducer is turned about a center point of its active face. Namely, the ultrasound transducer unit 19 is rotatable about an axis which is disposed perpendicularly to the axis of the catheter member 3.

In order to turn the ultrasound transducer unit 19, a pair of rotation transmission wires 20 are lapped in and around an annular groove 12a on the circumference of the follower pulley 12 from opposite directions and securely fixed to the latter at the respective fore ends. On the rear side of the ultrasound transducer unit 19, these rotation transmission wires 20 are led into the angle section 3b via pipes 21 and extended as far as the manipulating probe head 2 through the flexible body 3a. of the catheter member 3. Between the proximal end of the pipe 21 and the manipulating probe head 2, the wires 20 are received in coil sleeves 22 each in the form of a metal wire coil with tightly wound helices. Fore ends of the coil sleeves 22 are connected to the pipes 21 which are fixedly mounted in position within the casing 10, while rear ends of the coil sleeves 22 are securely connected to a rotational drive within a housing of the manipulating probe head 2 as will be described below.

Within the housing of the manipulating probe head 2, the rotation transmission wires 20 which are led out of the coil sleeves 22, as illustrated in FIG. 4, are wrapped in and around an annular groove 23a on the circumference of a drive pulley 23 and securely fixed to the latter at the respective proximal ends. The drive pulley 23 is coupled with an inner end of a rotational shaft 24 the outer end of which is projected out of the housing of the manipulating head assembly 2 and provided with an operating knob 25 to be manipulated by an operator. Therefore, upon turning the knob 25 with fingers, the rotation transmission wires 20 are pulled back and forth in step with rotation of the drive pulley 23, causing the follower pulley 12 to rotate substantially in synchronism with the drive pulley 23. In order to detect the rotational angle of the follower pulley 12, a bevel gear 26 which is provided on the circumference of the drive pulley 23 is meshed with a bevel gear 28 which is in turn coupled with an input shaft 27a of an encoder 27. Therefore, upon turning the drive pulley 23, its rotational angle is detected by the encoder 27 to determine the direction of ultrasound scanning.

By pulling the rotation transmission wires 20 back and forth, the transducer 11 of the ultrasound transducer unit 19 is turned and shifted into a different angular position to make an ultrasound scanning in a different direction or plane. In this regard, since the ultrasound transducer unit 19 is mounted on the follower pulley 12 which has its rotational axis disposed perpendicularly to the axis of the distal end section 3c of the catheter member 3, the direction of an electronic sectoral scanning by the ultrasound transducer 11 lies in a direction perpendicular to the axis of the distal end section 3c. In addition, by bending the angle section 3b which is connected to the distal end section 3c of the catheter member 3, the ultrasound transducer 11 on the distal end section 3c can be turned into an arbitrary direction. Accordingly, through operation of the angle section 3b, the distal end section 3c with the ultrasound transducer 11 can be turned toward a diseased portion or other intracavitary regions of particular interest for ultrasound examination. In case an intracavitary wall to be examined exists at a large angle with the direction of insertion of the catheter member 3, however, there may arise a situation where the operator finds it difficult to locate the ultrasound transducer 11 in an appropriate position in terms of ultrasound scanning range, depending upon positional relations between the path of insertion of the catheter member and the intracavitary region of interest. Besides, although it is desirable for ultrasound signals from the ultrasound transducer to enter an intracavitary wall with an angle of entrance of substantially 90 degrees, difficulties are often experienced in controlling the angle of entrance simply by repositioning the catheter member 3 as a whole or by bending the angle section 3b within an internal canal or the like.

SUMMARY OF THE INVENTION

With the foregoing situations in view, it is an object of the present invention to provide a multi-plane electronic ultrasound probe which can adjust the scanning position or direction of an ultrasound transducer accurately in an extremely facilitated manner.

It is another object of the present invention to provide an ultrasound probe of the sort as mentioned above, which is provided with a tilt mechanism which can tilt an active face of an ultrasound transducer in a desired direction, permitting to make fine adjustments of an ultrasound scanning range of an ultrasound transducer very easily.

In accordance with the present invention, the above-stated objectives are achieved by the provision of a multi-plane electronic ultrasound probe which basically includes a manipulating probe head, an elongated catheter member extended out from the manipulating probe head, an ultrasound transducer rotatably supported by a rotary member within a casing on a distal end section of the catheter member and having a large number of ultrasound transducer elements in a row on the rotary member, a rotation control knob provided on the manipulating probe head to control rotation of the rotary member through rotation transmission wires extended between the rotation control means and the rotary member through the catheter member via a drive pulley mounted on the manipulation probe head: the ultrasound probe comprising a tilt mechanism for tilting a rotational axis of the rotary member thereby to tilt an active face of the ultrasound transducer in a predetermined direction, the tilt control mechanism including a tilt control means provided on the manipulating probe head, a tiltable support for the rotary member, and a tilt signal transmission means for transmitting a tilt signal from the tilt control means to the tiltable support member.

In tilting the ultrasound transducer on the distal end section of the catheter member, it is desirable for the tilt mechanism to be arranged to tilt the axis of rotation of the ultrasound transducer in the axial direction of the catheter member, and more preferably forwardly in the axial direction within a predetermined angular range from a normal position where the rotational axis of the ultrasound transducer is disposed in a perpendicularly intersecting relation with the axis of the catheter member.

In one specific form of the invention, the tilt mechanism includes a remote-control rocking seat for the rotary member which supports the ultrasound transducer. Normally, the rocking seat is retained in a predetermined angular position by means of a spring or other biasing means, and tilted by way of a tilting wire against the action of the biasing spring. The tilting wire serves to transmit tilt signals from an tilt control means on the manipulating head of the ultrasound probe, and, for this purpose, the tilting wire is extended through the entire length of the catheter member and, within the manipulating head assembly, connected the tilt control means which produces tilt drive signals through the tilting wire.

In one specific form of the invention, the tilt control means is provide in the form of a wire retractor including a reciprocating member connected to the tilt signal transmission wire and axially displaceably engaged with a screw member, and a tilt control ring fixedly provided at an outer end of the reciprocating member and partly exposed on the outer side of a housing of the manipulating head.

In another preferred form of the invention, the ultrasound probe includes a tilt control cable encasing a tilt signal transmission wire in a flexible coil sleeve between the distal end section of the catheter member and the manipulating head, and a wire bundling case fitted in a flexible body portion of the catheter member and having an inner case and an outer case substantially in coaxial relations with each other. The wire bundling case holds the tilt control cable within the inner case along with rotation transmission wires to and from the rotary member, while holding a large number of signal cables to and from the ultrasound transducer within the outer case in such a manner as to circumvent the tilt and rotation control cables in the inner case. Preferably, the inner case of the wire bundling case is constituted by a flexible tube holding the tilt and rotation control cables in a loose state, and the outer case is constituted by a tape wrapping loosely wound around the signal cables.

BRIEF DESCRIPTION OF THE DRAWINGS

The above and other objects, features, effects and advantages of the invention will become apparent from the following description, taken in conjunction with the accompanying drawings which show by way of example some preferred embodiments of the invention and in which.

DESCRIPTION OF PREFERRED EMBODIMENTS

Figure 5:
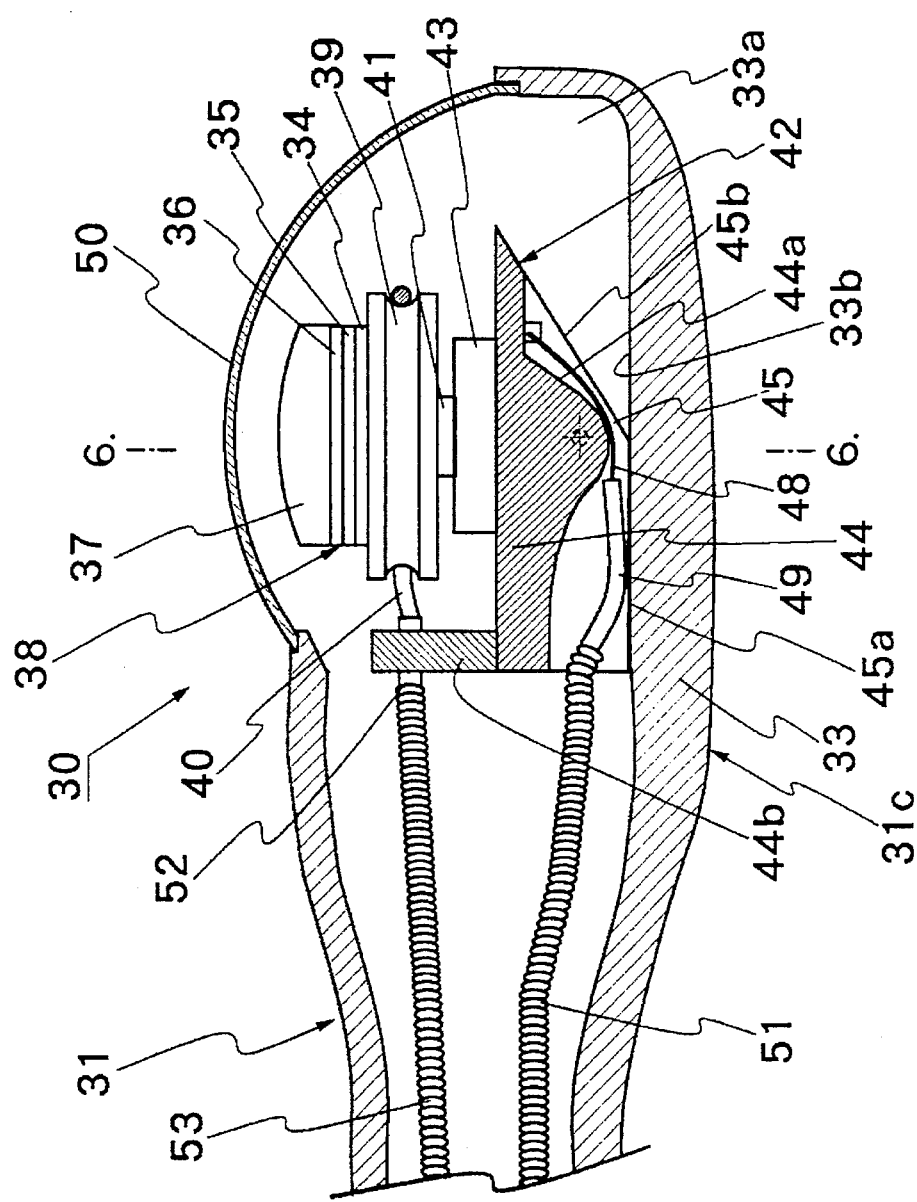
FIG. 5 is a schematic sectional view of a distal end section of a catheter member of a multi-plane electronic ultrasound probe embodying the present invention.
Figure 9:
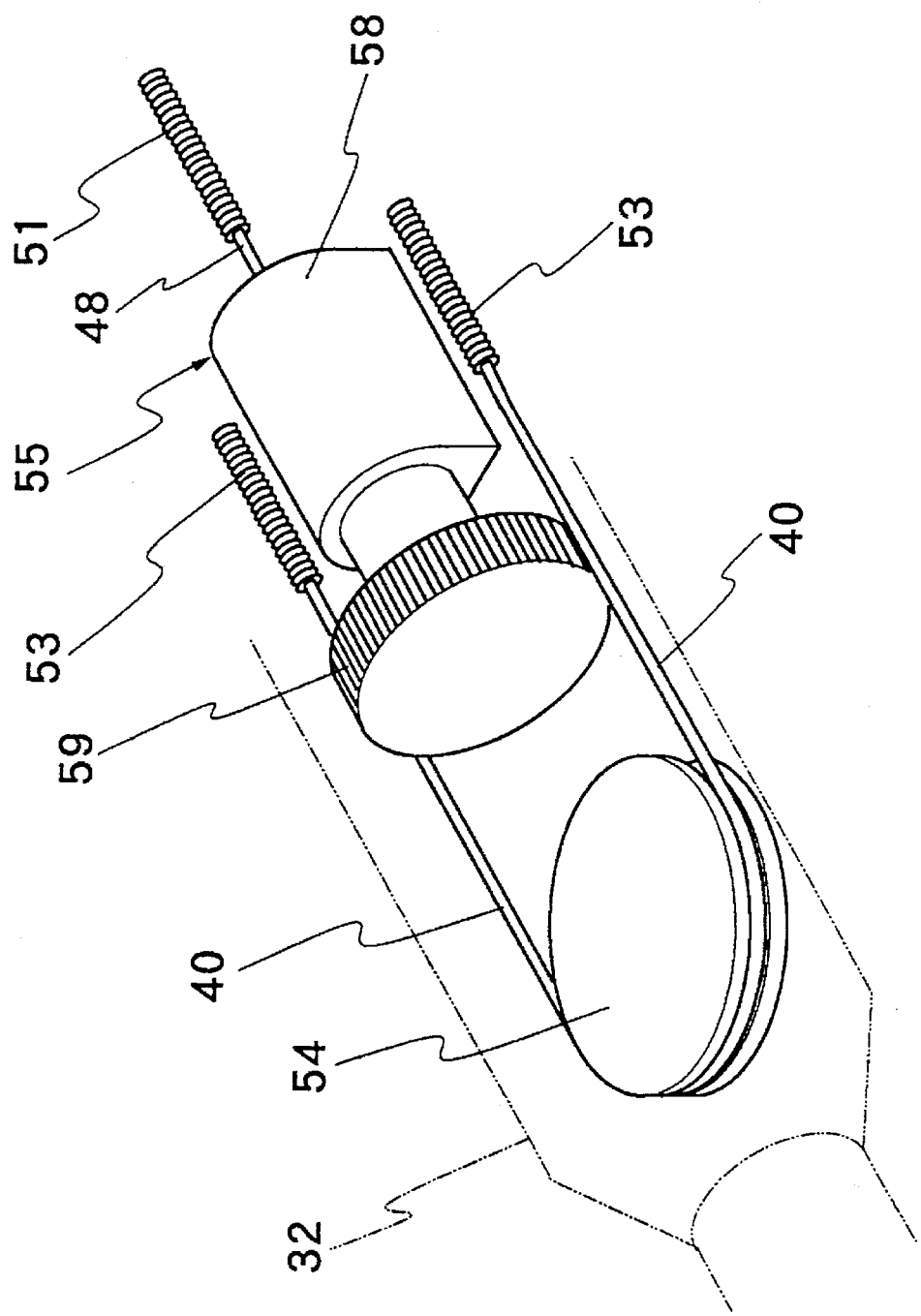
FIG. 9 is a schematic illustration explanatory of rotation transmission wires and tilting wire drive mechanisms on a manipulating head of the probe.
Figure 14:
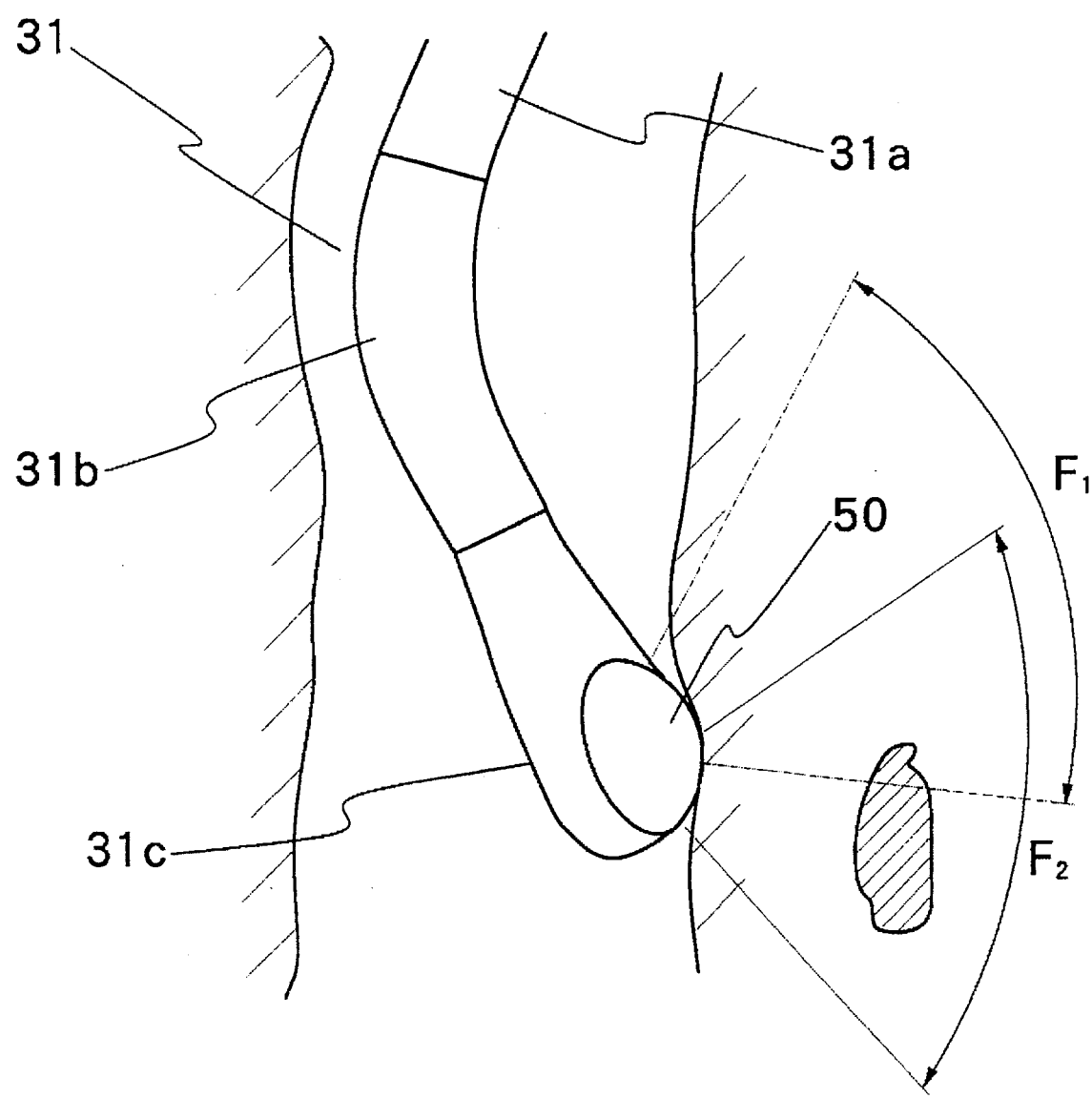
FIG. 14 is a schematic illustration explanatory of adjustments of an ultrasound scanning range.

Hereafter, the invention is described more particularly by way of its preferred embodiments with reference to the accompanying drawings. Referring first to FIG. 5, there is shown a distal end portion of a catheter member 31 of an ultrasound probe 30 incorporating a tilt mechanism according to the invention. The catheter member 31 includes an elongated flexible body 31a which is extended out from a manipulating probe head 32 (FIG. 9), and an angle section 31b and a distal end section 31c which are successively connected to the fore end of the flexible body 31a (FIG. 14). The distal end section 31v is provided with a casing 33 which internally defines a closed chamber 33a to accommodate therein an ultrasound unit 38 including a transducer 35 for linear and sectoral electronic scanning, packing material 34 underlying the ultrasound transducer 35, an acoustic matching layer 36 laminated on the ultrasound transducer 35, and an acoustic lens 37 laminated on top of the acoustic matching layer 36. The packing material 34 of the ultrasound unit 38 is securely fixed on a follower pulley 39 which serves as a rotary member for turning the ultrasound unit 38. A pair of rotation transmission wires 40 are wrapped around the follower pulley 39 in such a way that the angular scanning direction of the ultrasound transducer 35 is shifted in the rotational direction by pulling back and forth the rotation transmission wires 40. To this point, the arrangements of the rotational drive mechanism for the ultrasound transducer has no significant differences from the prior art counterpart shown hereinbefore.

Figure 6:
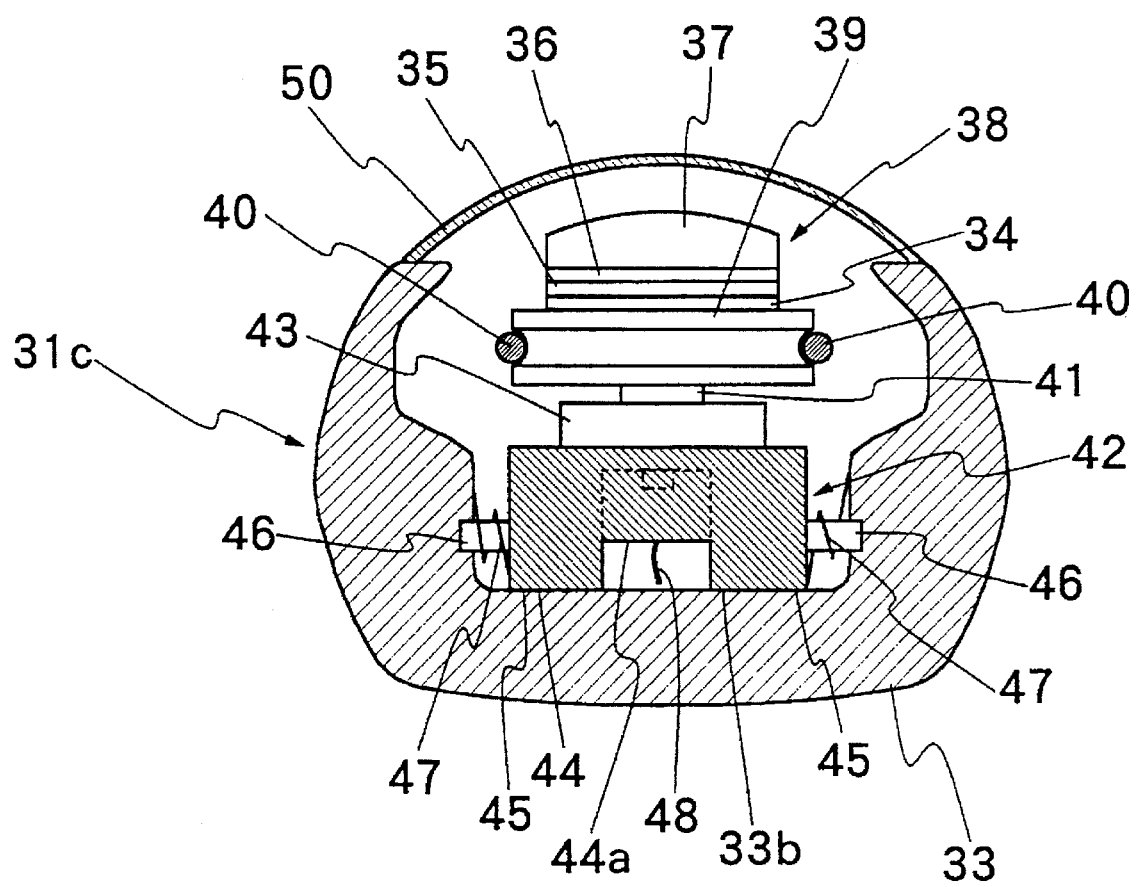
FIG. 6 is a schematic sectional view taken on line X—X of FIG. 5.
Figure 7:
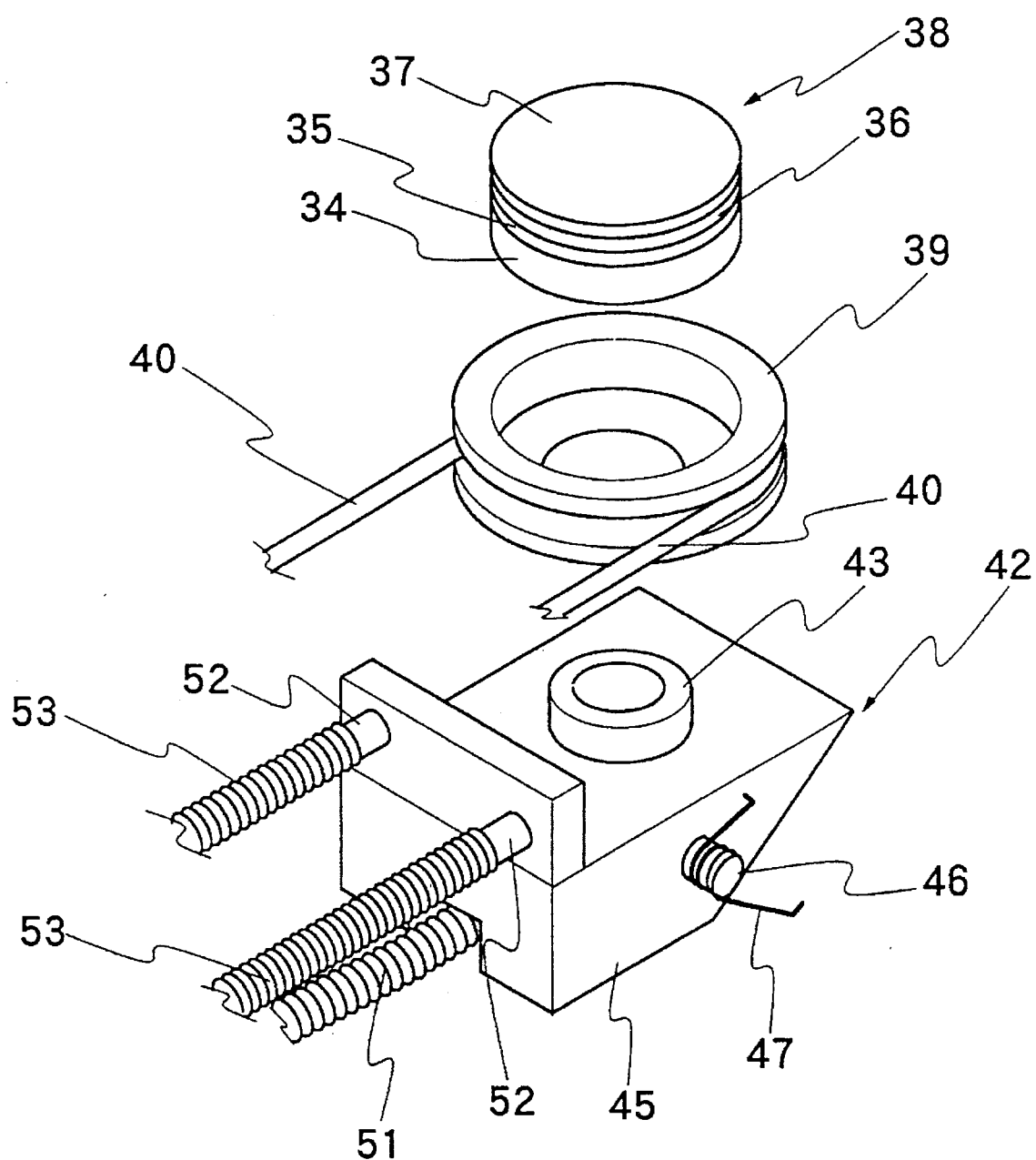
FIG. 7 is a schematic perspective view of an ultrasound transducer on a tilt mechanism, partly shown in a disassembled state.

As clear from in FIGS. 6 and 7, a rotational shaft 41 which is projected on the lower side of the follower pulley 39 is rotatably supported on a rocking seat 42 through a bearing member 43. The just mentioned rocking seat 42 is constituted by an upper plate portion 44 with the bearing 43 on its top side, and a pair of side plate portions 45 which are provided at the opposite lateral sides of the upper plate portion 44. Each one of the side plate portions 45 is provided with a flat sole 45a on the lower side parallel with the upper plate portion 44 substantially up to a middle point from its rear end, and an oblique undercut surface 45 rising upward toward its front end. Projected laterally outward from the two side plate portions 45 are rocking pins 46 at positions above and in the vicinity of the middle points where the fore ends of the flat soles 45a meet the lower ends of the oblique undercut surfaces 45b. These rocking pins 46 are pivotally supported on inner wall portions of the casing 33 to tilt the rocking seat 42 in a predetermined direction as will be described hereinlater.

Figure 8:
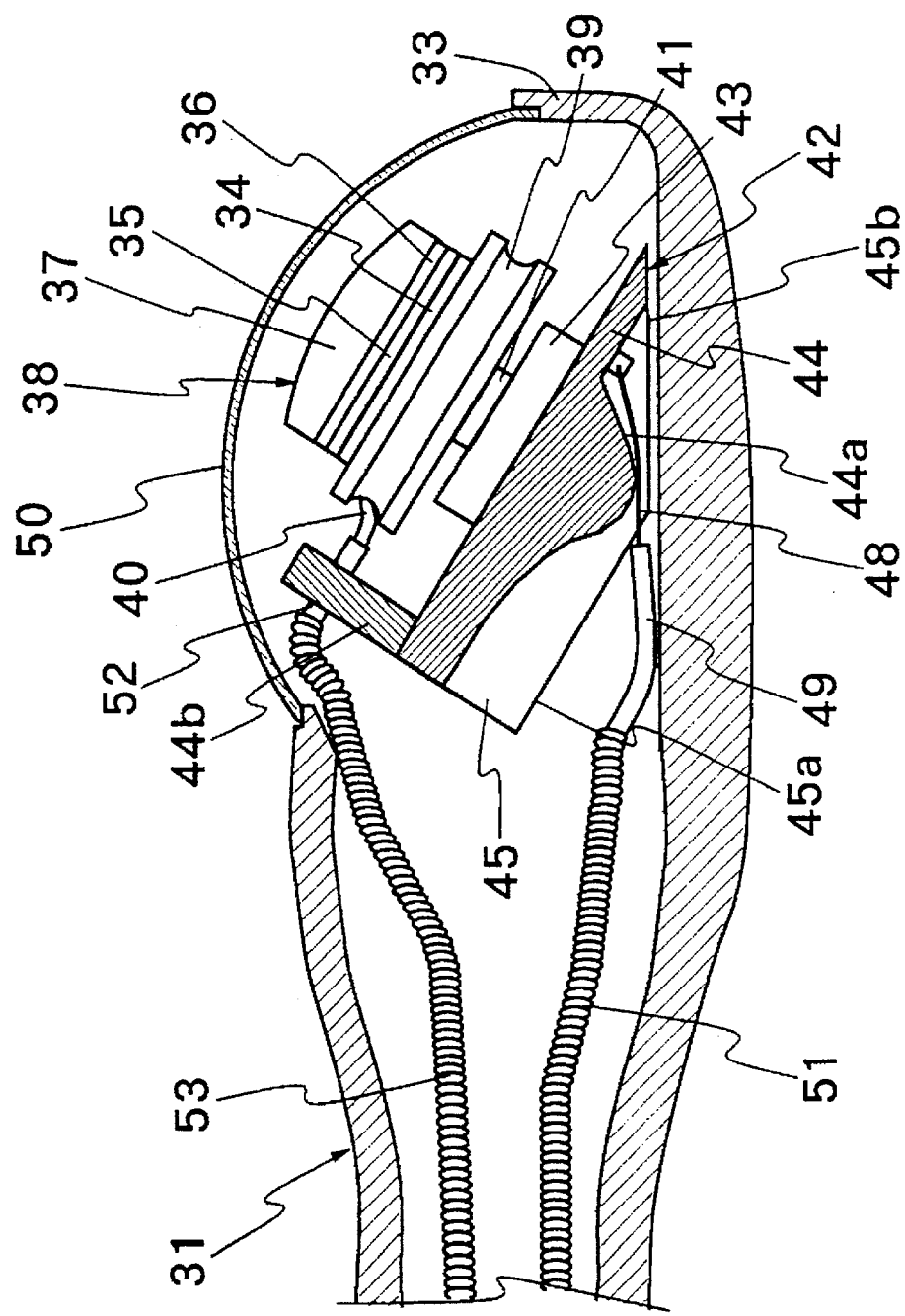
FIG. 8 is a view similar to FIG. 5 but showing a rocking seat for a rotary member in an inclined state.

Mounted on the rocking pins 46 of the rocking seat 42 are biasing springs 47 which normally hold the flat soles 45a of the side plates 45 in abutting engagement with bottom wall surfaces 33b of the casing 33 as shown in FIGS. 5 and 6. When a downward pushing force is exerted on a fore end portion of the rocking seat 42, however, the oblique undercut portions 45b of the side plates 45 are brought into abutting engagement with the bottom wall 33b of the casing 33, turning the rocking seat 42 into a tilted posture against the biasing forces of the springs 47 as shown in FIG. 8. For tilting the rocking seat 42, a tilting wire 48, which serves as a tilt signal transmission means, is connected to the lower side of the rocking seat 42 in a fore end portion thereof. More specifically, from the fore end of the rocking seat 42, the tilting wire 48 is routed downward along a guide portion 44a on the lower side of the upper plate 44 to a position beneath the rocking pins 46 and then passed through a tubular guide member 49 which is securely fixed on the bottom wall 33b of the casing 33. Accordingly, upon pulling the tilting wire 48, the rocking seat 42 is tilted forward about the rocking pins 46.

Upon tilting the rocking seat 42, the ultrasound unit 38 as a whole is tilted together with the follower pulley 39. In order to make ultrasound scans by the ultrasound transducer 35 feasible even in a tilted position, the casing 33 is provided with an acoustic window 50 which is elongated in the forward direction to such an extent as to permit transmission and reception of ultrasound signals therethrough even when the ultrasound unit 38 is tilted to a maximum angle of inclination. The acoustic lens 37 as well as the acoustic window 50 is formed in a hemispheric shape which is concentric with tilting movements of the rocking seat 42.

The tilting wire 48 from the rocking seat 42 is extended up to the manipulating probe head 32 through a coil sleeve 51, which is constituted by a tightly wound wire coil and connected to the proximal end of the guide pipe 49. The guide tube 49 is securely fixed on the bottom wall 33b of the casing 33 as mentioned above. Similarly, the paired rotation transmission wires 40 from the follower pulley 39 are extended up to the manipulating head 32 through guide pipes 52 which are securely fixed in a riser portion 44a of the upper plate 44 of the rocking seat 42 and through coil sleeves 53 of tightly wound wire coils which are connected to the proximal ends of the guide pipes 52.

Figure 1:
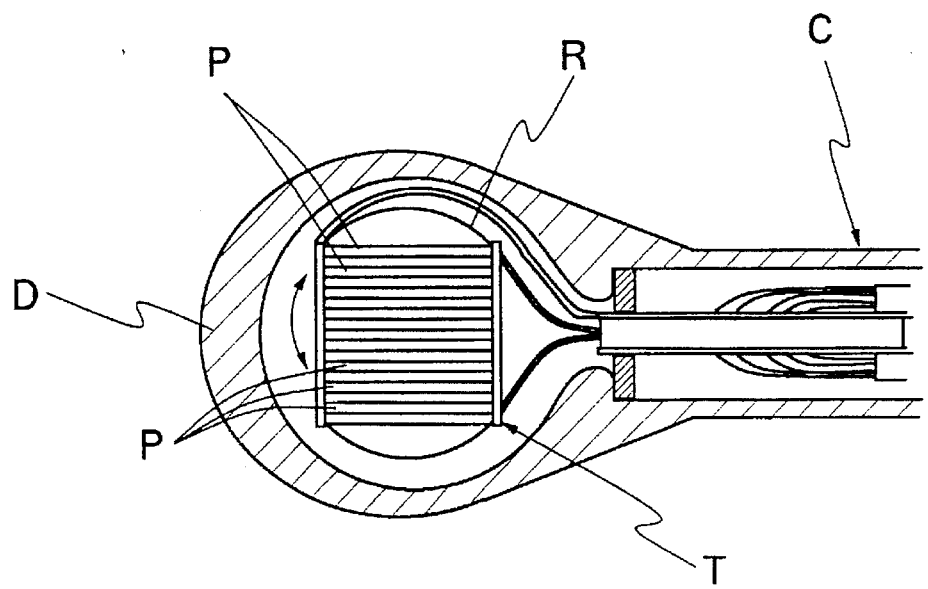
FIG. 1 is a schematic illustration of a distal end portion of an ultrasound probe with a multi-plane electronic scan transducer.
Figure 2:
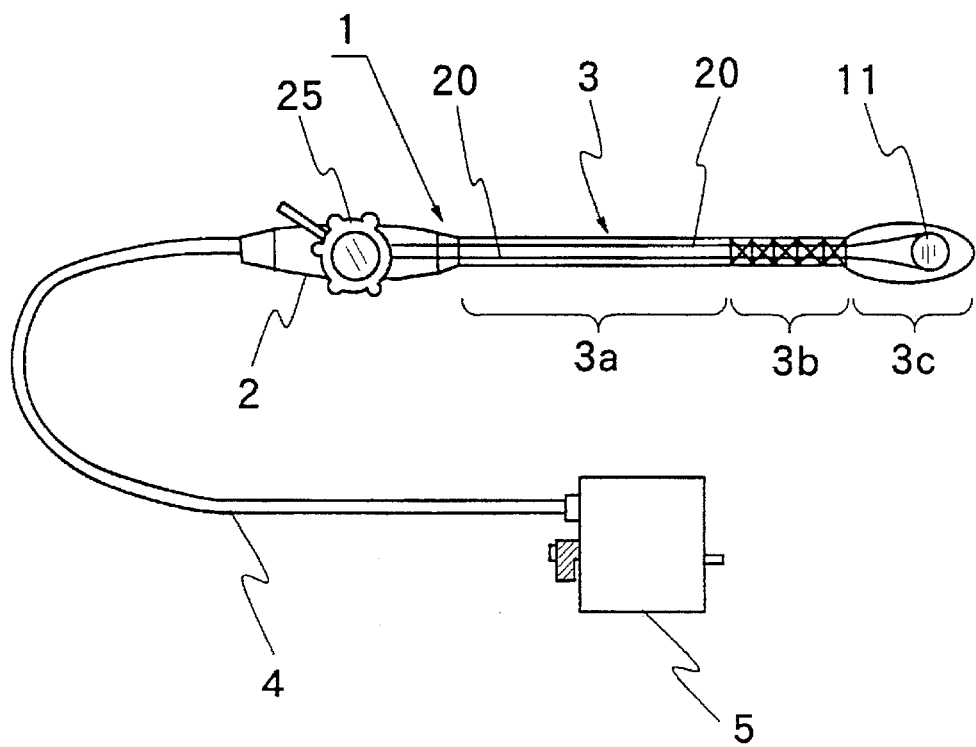
FIG. 2 is a schematic view of a prior art multi-plane electronic ultrasound probe, showing its general layout.
Figure 3:
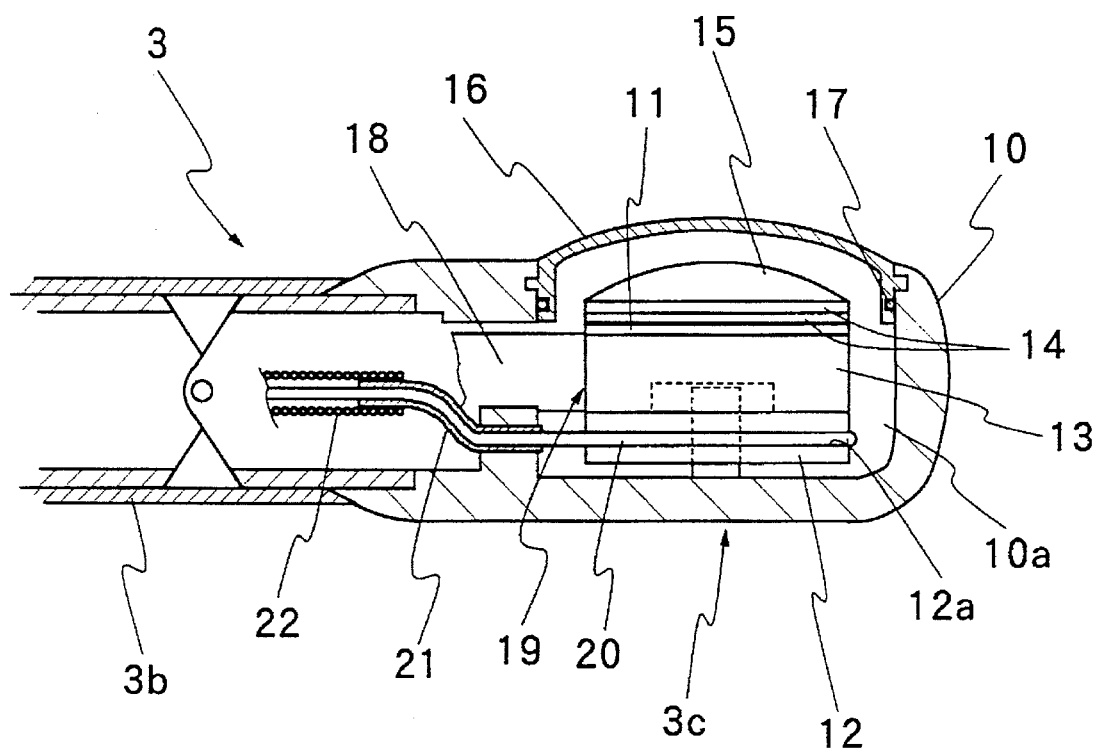
FIG. 3 is a schematic sectional view of a distal end section of a catheter member of the probe of FIG. 2.
Figure 4:
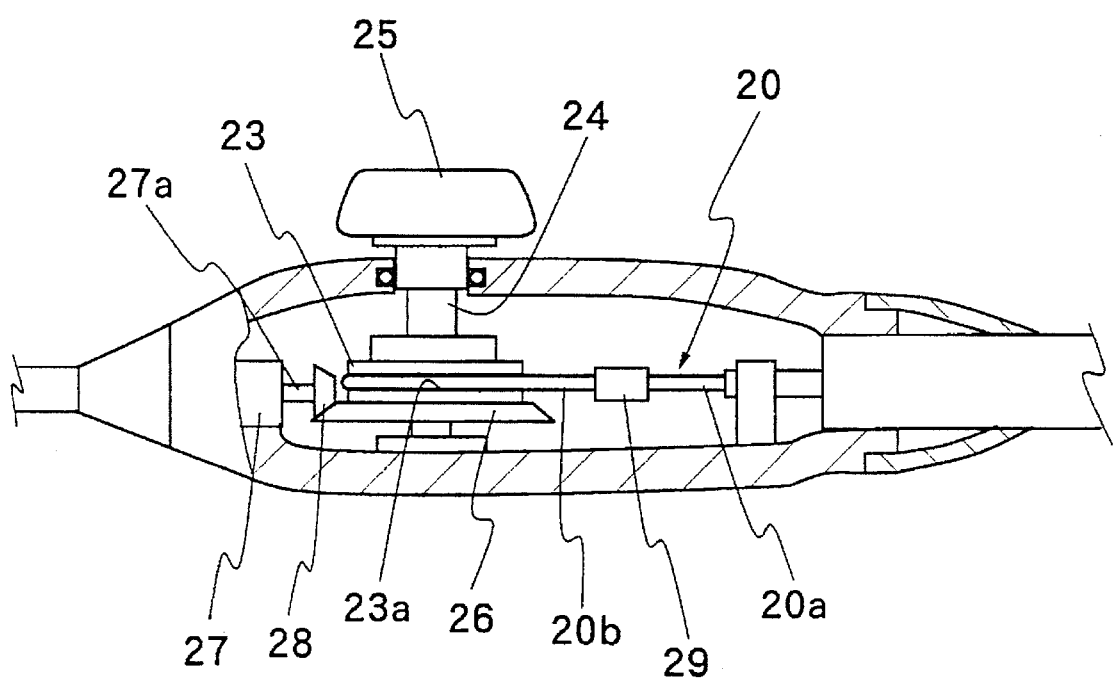
FIG. 4 is a schematic sectional view of a manipulating head of the probe of FIG. 2.

Within the housing of the manipulating probe head 32, the rotation transmitting wires 40 are wrapped around a drive pulley 54 while the tilting wire 48 is connected to a tilting wire retractor 55. The rotation transmission wires 40 are led out through coil sleeves 53, which are securely fixed to a stationary structure of the manipulating probe head 32, and wrapped around the drive pulley 54. Accordingly, upon turning the drive pulley 54, the rotation transmission wires 40 are pulled back and forth to turn the follower pulley 39 substantially in synchronism with the drive pulley 54, as a result driving the ultrasound unit 38 to turn about the rotational shaft 41. In this case, the drive pulley 54 is coupled with an operating knob, which is provided on the housing of the manipulating probe head 32, and with an encoder substantially in the same manner as in the prior art counterpart shown in FIGS. 2 to 4. Further description on the arrangements of the operating knob and encoder is therefore omitted here.

Figure 10:
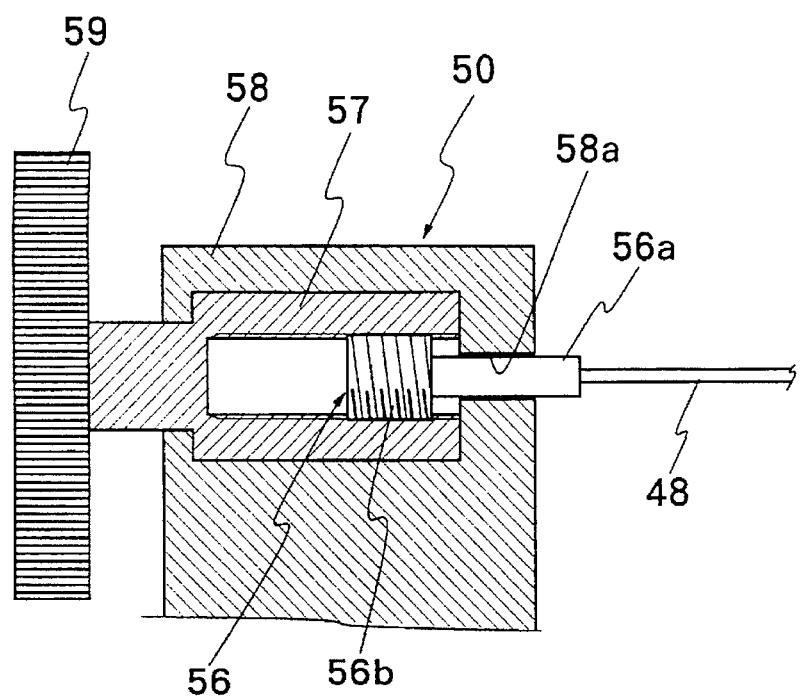
FIG. 10 is a schematic illustration of a tilting wire retractor provided on the manipulating head.

On the other hand, as seen in FIG. 10, the tilting wire retractor 55 is constituted by a reciprocating member 56, which is connected to the tilting wire 48 coming out of the proximal end of the coil sleeve 51. The reciprocating member 56 is provided with a square rod portion 56a and a male screw portion 56b which is in meshed engagement with a female screw member 57. The female screw member 57 is supported on a bearing member 58 which permits rotational movements but blocks axial movements of the female screw member 57, and provided with a tilt control ring 59 on its outer end in such a way that part of the tilt control ring 59 is exposed outside the manipulating head assembly 32. The bearing member 58 is provided with a square restrictive hole 58a through which the square rod portion 56a of the reciprocating member 56 is slidably projected to the outside of the bearing member 58. Accordingly, the reciprocating member 56 is movable in the axial direction but its rotational movement is blocked by the square restrictive hole 58a. With these arrangements, if the tilt control ring 59 is turned with fingers of the operator's hand which grips the manipulating head 32, the reciprocating member 56 is retracted into or protruded out of the female screw member 57 according to the direction of rotation of the operating ring 59, thereby pulling backward or forward the tilting wire 48 to turn the rocking seat 42 into or out of a tilted position. Fine adjustment of the inclination angle is feasible in case the male and female screw members 56b and 57 engaged with each other through fine-pitched screw threads.

Figure 11:
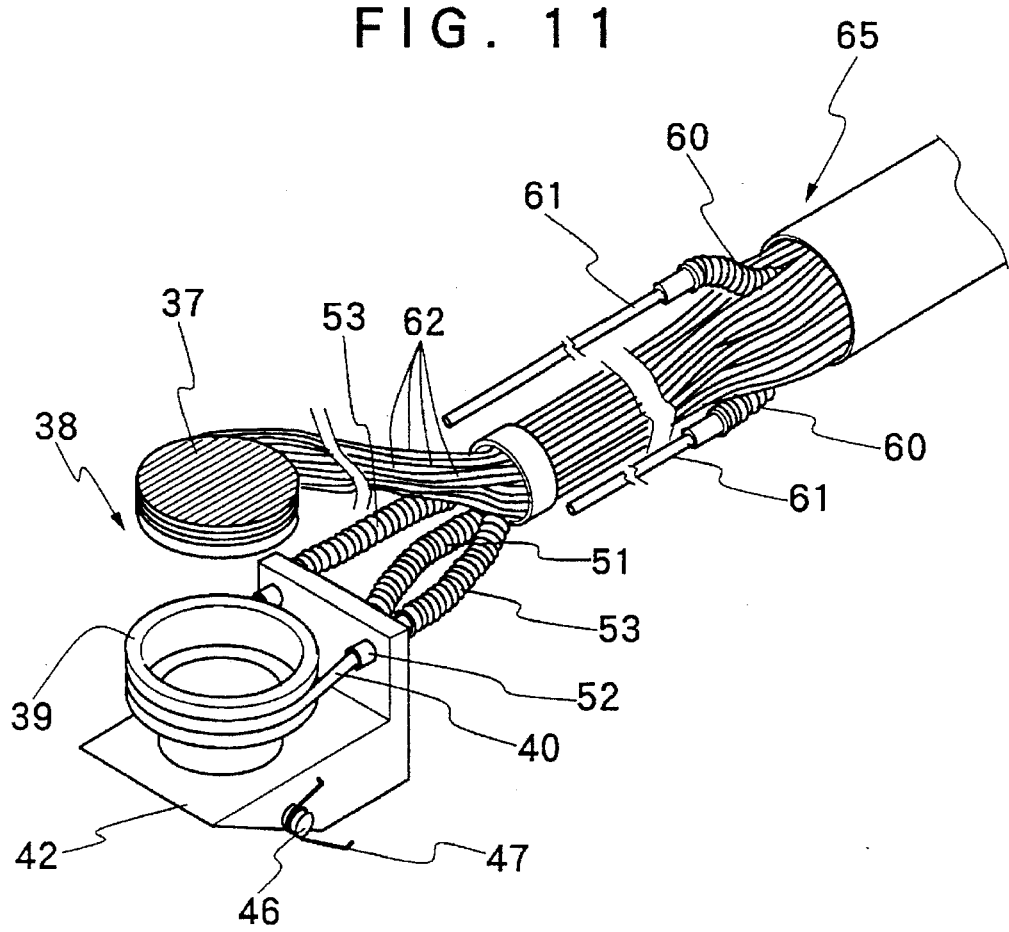
FIG. 11 is a schematic illustration of a wire bundling case construction assembling together various cables to and from the distal end section of the catheter member.

As shown in FIG. 11, the catheter member 31 of the probe needs to accommodate a large number of cables to and from its distal end section 31C, including a control cable having the tilting wire 48 fitted in the flexible coil sleeve 51, a couple of control cables having the rotation transmitting wires 40 fitted in the coil sleeves 53 and at least a couple of angling control cables having angling wires 61 fitted similarly in a couple of flexible coil sleeves 60. Besides, for electronic scanning operations by the ultrasound transducer 36, the catheter member 31 needs to accommodate a large number of signal cables (not shown in FIGS. 5 through 8) to and from the ultrasound transducer 36. If all of these cables are encased in the catheter member 31 in a loose state, it is very likely that they will get entangled with each other when the catheter member 31 is flexed along a path of insertion into an intracavitary site of examination, with possibilities of breaking damages to the fragile signal cables 52. Besides, at the time of flexure of the catheter member 31, the rotation transmitting wires 40, tilting wire 48 and angling wire 61 on the outer side of a bend could be subjected a pulling force if they are located close to inner surfaces of a tubular casing of the flexible body 31a of the catheter member 31. Therefore, it is preferable for these wires 40, 48 and 61 to be located as close to the center of the catheter member 31 as possible.

Figure 12:
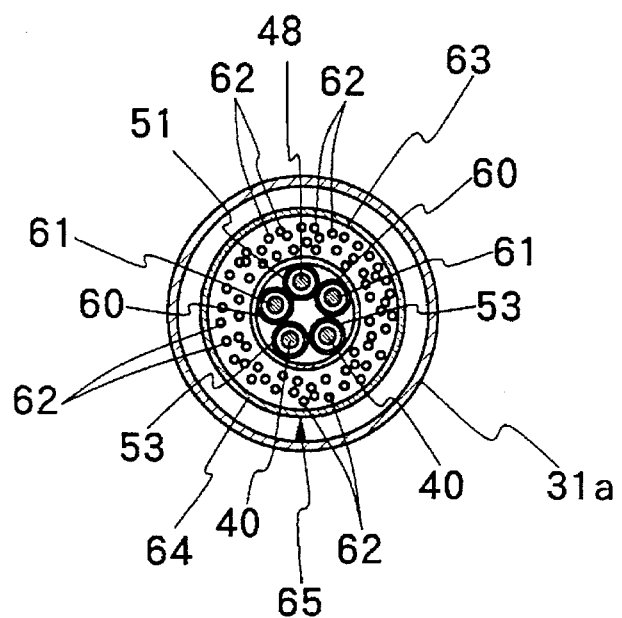
FIG. 12 is a schematic sectional view of a flexible body of the catheter member.

In this regard, as shown particularly in FIG. 12, the catheter member 31 employs a coaxial wire bundling case 65 having an inner case 63 and an outer case 65 for holding a large number of cables in a suitably protected state within the elongated flexible body 31a. The inner casing 63 receives therein the rotation transmitting wires 40 and the angling wires 61 in the coil sleeves 53 and 60 along with the tilting wire 48 in the coil sleeve 51. On the other hand, a large number of signal cables 62 are placed around the inner case 63 in such a way as to circumvent the latter within the outer case 64. Consequently, by means of the wire bundling case 65, a large number of cables are encased in the form of a single bundle substantially over the entire length of the elongated flexible body 31a of the catheter member 31.

The inner case 65 of the wire bundling case 65 is fitted in a center position in a moderately loose state in order to avoid stiffening of the control cables 35 and 36. Similarly, preferably the outer case 64 is arranged to enshroud the signal cables 62 in an appropriately loose state. To this end, it is desirable to use a flexible tube for the inner case 63 and a tape wrapping for the outer case 64. The wire bundling case 65 should be arranged in a form which is satisfactory in flexibility and shape retainability and less bulky especially in diameter. If arranged in this way, the wires 40, 48 and 61 are located substantially in a center position of the flexible body 31a of the catheter member 31, so that they are less susceptible to a pulling force even when the flexible body 31a is bent to a large extent, and the coil sleeves 51, 53 and 60 are freed from possibilities of entangling with the signal cables 62.

In an ultrasound scanning operation, after introducing the catheter member 31 of the ultrasound probe 30 into an aimed position within an internal canal or the like, the ultrasound transducer 35 is activated for an ultrasound scan in the manner well known in the art to obtain an ultrasound image of a tomographic plane through an intracorporeal region or an organ to be examined. Then, by turning the drive pulley 54 through a certain angle, the active signal transmission and reception face of the ultrasound transducer 53 is correspondingly turned into a different angular direction and put in operation again to make an electronic ultrasound scan in that angularly shifted position. The so-called multi-plane ultrasound images can be obtained by repeating such a tomographic ultrasound scanning operation successively at a number of angularly shifted positions, in order to grip three-dimensionally the whole image of a subject under examination, for example, the whole image of the heart.

Figure 13:
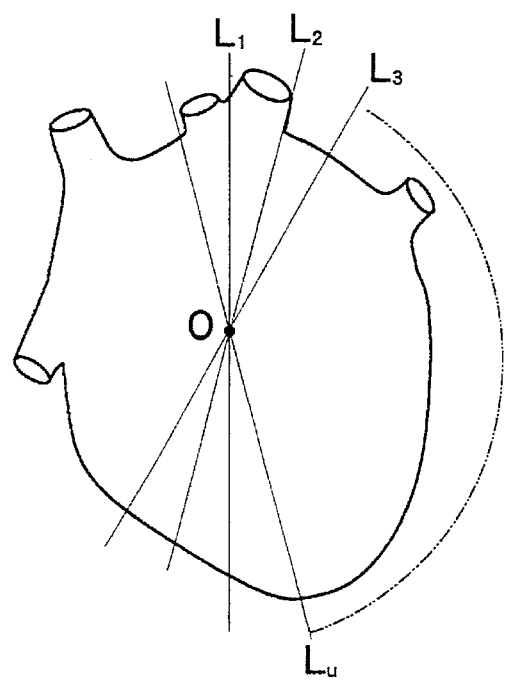
FIG. 13 is a schematic illustration explanatory of cardiac ultrasound scanning with a multi-plane electronic ultrasound transducer.

In such a multi-plane scanning operation, the ultrasound transducer 31 is turned about the rotational shaft 41 which is disposed in a direction perpendicular to the axis of the distal end section 31c of the catheter member 31. Accordingly, in the case of a multi-plane ultrasound scanning operation on the heart as shown in FIG. 13, for example, firstly the axis of the rotational shaft 41 is located on an extension line through an approximate central point 0 of the heart to obtain a tomographic ultrasound image on the scanning line $L_1$, repeating the ultrasound scan successively on angularly shifted scanning lines $L_2$ and $L_3$ through $L_n$ to obtain tomographic ultrasound images which are helpful in gripping the whole image of the heart. For this purpose, there often arise necessities for moving the catheter member 31 as a whole back and forth within an internal canal or the like or for bending the angle section 31b to turn the ultrasound transducer into a desired direction for examination. However, in some cases accurate control of the ultrasound scanning position and direction is found difficult to achieve simply by operation of the angle section 31b because of peculiar positional relations between the catheter member 31 inserted into an internal cavity and an intracavitary wall to be scanned.

In this regard, instead of being directly mounted within the casing 33 of the distal end section 31c, the ultrasound unit 38 is supported on the rocking seat 42 which can be tilted forward in the axial direction of the distal end section 31c of the catheter member 31 by pulling the tilting wire 48, and the operator can pull the tiling wire 48 in a forward or backward direction whenever necessary by turning the operating ring 59 in such a direction as to retract or propel the reciprocating member 56 into or out of the female screw member 57 along with the tilting wire 48. Accordingly, through manipulation of the operating ring 59, the operator can make fine adjustments of the position and direction of an ultrasound scanning range smoothly.

More specifically, the ultrasound probe has a Scanning range $F_1$ as indicated by imaginary line in FIG. 14 when simply the angle section 31b of the catheter member 31 alone is bent toward an intracavitary wall of interest within an internal canal or the like, deviated to some extent from a diseased portion which needs ultrasound scanning. In such a case, by pulling the tilting wire 56 inward, the position of the ultrasound transducer is shifted to have a forwardly shifted scanning range F2 which completely covers the diseased portion as indicated by solid line in the same figure. It follows that, the position or direction of the ultrasound transducer 35 can be accurately adjusted into an appropriate position relative to an intracavitary wall to be scanned, simply by turning the tilt control ring 59 after introducing the distal end section 31c of the catheter member 31 into a site approximately near the scanning intracavitary wall. In addition, the rocking seat 42 can be retained in a tilted position without continuedly holding the control ring 59 with fingers after an adjustment, by weakening the biasing force of the return spring 47 to a minimum necessary force which can ensure smooth return actions of the rocking seat 42 upon removing therefrom a pulling force exerted through the tilting wire 48, while engaging the female screw member 57 with the bearing member 58 through a certain degree of sliding resistance.

Further, the rotation transmission wires 40, which are wrapped around the follower pulley 39, are passed through the guide pipes 52 which are fixedly mounted on the rocking seat 42. Therefore, even if the rotational axis of the follower pulley 39 is tilted as a result of a tilting operation on the rocking seat 42, there is no possibility of the tilting operation causing changes in positional relations between the rotation transmission wires 40 and the follower pulley 39, that is to say, changes in wrapping directions of the wires 40 relative to the follower pulley 39. Namely, the rotation of the follower pulley 39 can be controlled smoothly through the rotation transmission wires 48 in multi-plane ultrasound scanning operations, without experiencing degradations in rotation controllability or positional deviations of the rotation transmission wires 48.

Although the rocking seat is arranged to be tilted forward in the axial direction of the distal end section of the catheter member in the above-described embodiments, of course it may be arranged to be tiltable back and forth in the axial direction of the distal end section if desired. Further, instead of rotating the follower pulley by a couple of rotation transmission wires, for example, a single wire may be used in combination with a spring member or the like which is arranged to urge the follower pulley into a predetermined angular position. Moreover, as a tilt control mechanism for the rocking seat, an electric motor or the like may be incorporated into the distal end section of the catheter member for driving same in a tilting direction in response to a signal from a tilt control means provided on the manipulating head. In such a case, a signal cable between the motor and the tilt control means serves as a signal transmission means.

What is claimed is:

1. A multi-plane electronic scan ultrasound probe having a manipulating head, an elongated catheter member extended out from said manipulating head on a front bide thereof, an ultrasound transducer rotatably mounted within a casing on a distal end section of said catheter member and having a row of a large number of ultrasound transducer elements on a rotary body, a rotation control knob provided on said manipulating head to control rotation of said rotary member through rotation transmission wire means extended between said rotation control means and said rotary member through said catheter member via a drive pulley mounted on said manipulation head: said multi-plane electronic ultrasound probe comprising a tilt control mechanism for tilting rotational axis of said rotary member thereby to turn an active face of said ultrasound transducer in a predetermined direction, said tilt control mechanism including a tilt control means provided on said manipulating head, a tiltable support for said rotary member, and a tilt signal transmission means connected between said tilt control means and said tiltable support to transmit a tilt signal to said latter.

2. A multi-plane electronic scan ultrasound probe as defined in claim 1, wherein said tilt control mechanism comprises a rocking seat rotatably supporting said rotary member thereon, a biasing means constantly urging said rocking seat toward a normal position, a tilt signal transmission wire connected between a wire retractor provided on said manipulating head and said rocking seat to tilt the latter against the action of said biasing means.

3. A multi-plane electronic scan ultrasound probe as defined in claim 2, wherein said rocking seat is arranged to be tilted in the axial direction of said catheter member.

4. A multi-plane electronic scan ultrasound probe as defined in claim 3, wherein said rocking seat is so positioned on said distal end section of said catheter member as to hold an active face of said ultrasound transducer normally in the axial direction of said catheter member in cooperation with said biasing means, and urged into a tilted position through a rocking movement upon pulling said tilt signal transmission wire by way of said wire retractor on said manipulating head.

5. A multi-plane electronic scan ultrasound probe as defined in claim 2, wherein said casing on said distal end section of said catheter member is provided with an acoustic window of a hemispheric shape concentric with the rocking movement of said rocking seat.

6. A multi-plane electronic scan ultrasound probe as defined in claim 1, wherein said wire retractor comprises a reciprocating member connected to said tilt signal transmission wire and axially displaceably engaged with a screw member, and a tilt control ring fixedly provided at an outer end of said reciprocating member and partly exposed on the outer side of a housing of said manipulating head.

7. A multi-plane electronic scan ultrasound probe as defined in claim 1, comprising a tilt control cable encasing a tilt signal transmission wire in a flexible coil sleeve between said distal end section of said catheter member and said manipulating head, and a wire bundling case fitted in a flexible body portion of said catheter member and having an inner case and an outer case substantially in coaxial relations with each other, said wire bundling case holding said tilt control cable within said inner case along with rotation transmission wires to and from said rotary member and holding a large number of signal cables to and from said ultrasound transducer within said outer case in such a manner as to circumvent said tilt and rotation control cables in said inner case.

8. A multi-plane electronic scan ultrasound probe as defined in claim 7, wherein said inner case of said wire bundling case is constituted by a flexible tube holding said tilt and rotation control cables in a loose state, and said outer case is constituted by a tape wrapping loosely wound around said signal cables.

* * * * *